United States Patent [19]
Manchak, III

[11] Patent Number: 5,435,176
[45] Date of Patent: Jul. 25, 1995

[54] HAZARDOUS WASTE CHARACTERIZER AND REMEDIATION METHOD AND SYSTEM

[75] Inventor: Frank E. Manchak, III, Santa Barbara, Calif.

[73] Assignee: Terranalysis Corporation, Santa Barbara, Calif.

[21] Appl. No.: 146,936

[22] Filed: Nov. 1, 1993

[51] Int. Cl.⁶ ............ E21B 49/08; E21B 49/00; E21B 7/00
[52] U.S. Cl. .................. 73/151; 73/864.43; 73/864.45; 175/50; 175/59; 175/21; 405/128; 405/263
[58] Field of Search .......... 73/31.03, 151, 152, 73/155, 863.11, 863.12, 864.43, 864.44, 864.45; 175/40, 50, 59, 21, 71; 405/128, 129, 131, 258, 263; 408/58, 59; 356/300, 326

[56] References Cited

U.S. PATENT DOCUMENTS

| | | | |
|---|---|---|---|
| 2,386,832 | 10/1945 | Zaikowsky | 73/863.11 |
| 3,042,124 | 7/1962 | Andersson | 73/864.44 |
| 3,255,353 | 6/1966 | Scherbatskoy | 250/254 |
| 4,694,437 | 9/1987 | Hanson | 367/27 |
| 4,776,409 | 10/1988 | Manchck, Jr. | 405/128 |
| 4,786,171 | 11/1988 | Lefebre et al. | 356/326 |
| 4,844,807 | 7/1989 | Manchak, Jr. | 405/128 |
| 4,844,839 | 7/1989 | Manchak, Jr. | 405/128 |
| 4,892,373 | 1/1990 | Sie | 385/12 |
| 4,901,069 | 2/1990 | Veneruso | 340/854.8 |
| 4,909,588 | 3/1990 | Harner et al. | 267/64.11 |
| 5,061,119 | 10/1991 | Balthaus et al. | 340/854.8 |
| 5,096,277 | 3/1992 | Kleinerman | 385/12 |
| 5,106,163 | 4/1992 | Fujiwara et al. | 299/1.3 |
| 5,135,058 | 8/1992 | Millgard et al. | 175/21 |
| 5,140,319 | 8/1992 | Riordan | 340/854.9 |

FOREIGN PATENT DOCUMENTS

| | | | |
|---|---|---|---|
| 7908089 | 5/1980 | Netherlands . | |
| 726335 | 4/1980 | U.S.S.R. . | |
| 92005338 | 4/1992 | WIPO | 73/864.43 |

Primary Examiner—Thomas P. Noland
Assistant Examiner—Michael J. Brock
Attorney, Agent, or Firm—Roth & Goldman

[57] ABSTRACT

A mobile hazardous waste characterization system having a top driven rotary kelly bar and drill bit in conjunction with a non-rotatable casing surrounding the kelly bar in which the casing and waste contamination sensing probes affixed thereto are supported by the top drive and are moved into and out of the site with the kelly bar and drill bit. The sensors preferably are optical soil contamination probes affixed to the casing to qualitatively and quantitatively determine soil contaminants and monitor remediation progress in situ at a subsurface soil characterization and treatment location. Soil gas sampling and a solid soil core sample removal device may be integrated with the optical contaminant sensing for accurate site characterization and simultaneous remediation thereof.

42 Claims, 11 Drawing Sheets

HAZARDOUS WASTE CHARACTERIZER AND REMEDIATION METHOD AND SYSTEM

BACKGROUND OF THE INVENTION AND PRIOR ART

The present invention relates to characterization of contaminated waste disposal sites and, more particularly, to real time analysis and monitoring prior to and during remediation treatment, of hazardous and/or radioactive waste contaminant levels and treatment progress. As used herein, the term "site" is intended in its broadest sense to include, but not be limited to, open and closed landfills, spill sites and even closed storage containers. Contaminants present in such sites are wide ranging in both type and concentration levels varying from organic, chlorinated and inorganic compounds and precious metals and in some cases mixtures thereof with radioactive materials ranging from low to intermediate radioactivity levels.

Past methods of gathering soil characterization data generally involve examination of vaporized or solid contaminant samples during in situ drilling including analysis, at the surface, of gas samples taken from the drilling elevation. When desired, solid core samples are removed and often transported substantial distances from the site where they are encountered to a remote laboratory for analysis. Such vapors and solids are believed to frequently undergo chemical and physical changes during their removal to and exposure at the soil surface. Accordingly, an in situ analysis of the contaminants and data indicating their precise location and with monitoring of the progress of chemical and/or physical treatment directly at the subsurface elevation where the contaminants are encountered and where treatment is taking place is required so that appropriate modifications of the treatment chemistry can be immediately made during treatment for most efficient remediation.

It is the primary object of the present invention to provide cost effective and efficient methods and systems for in situ real time analysis of hazardous and/or radioactive waste disposal sites and the simultaneous treatment thereof.

The invention involves placement of downhole probes which detect contaminants and monitor treatment progress and unique methods of subsurface working of contaminated soil with reduced motor torque loading as compared with the methods and apparatus known heretofore. Various types of probes, not critical to the broadest aspects of the invention are disclosed. The invention, in its broadest aspects, provides a method of identifying hazardous waste in a subsurface soil site comprising the steps of:

a) positioning contaminant sensing means proximate a sensing end of a nonrotatable drill casing having a first diameter;

b) boring a hole into the hazardous site using a rotary drill comprising a rotary kelly bar and a drilling section affixed to said kelly bar which creates a hole of a second diameter larger than said first diameter;

c) longitudinally inserting said sensing end of said non-rotatable casing and contaminant sensing means into said hole while boring said hole; and d) using said contaminant sensing means to sense the presence and composition of soil contaminants encountered during said boring of said hole while logging the characteristics of said contaminants and the locations at which they were encountered.

The invention further provides a hazardous waste characterization system comprising:

a) a soil boring apparatus which includes:
1) a rotatable drilling section;
2) a rotatable kelly bar having a first end affixed to said drilling section;
3) a motor for rotating said kelly bar and said drilling section, said motor being drivingly attachable to said kelly bar proximate a second end thereof; and
4) means for linearly moving said motor relative to a support therefor;

b) a non-rotatable casing surrounding said kelly bar and extending substantially the length thereof between said motor and said drilling section, said casing being affixed to and supported by said means for linearly moving said motor; and c) means affixed to said casing for sensing hazardous waste contaminants proximate the drilling section and for transmitting information to a location proximate the second end of the kelly bar, said drilling section being sized to create a bore larger than the cross section of said casing.

The invention further provides a hazardous waste characterization and soil remediation system comprising:

a) a soil boring apparatus having a rotatable drilling section, a rotatable kelly bar having a first end affixed to said drilling section and motor means drivingly attachable to said kelly bar proximate a second end thereof for rotating said kelly bar and drilling section;

b) a non-rotatable casing surrounding said kelly bar and extending substantially the length thereof between said motor means and said drilling section, said casing being affixed to and supported by said means for rotating;

c) means for axially moving said motor means and said casing;

d) conduit means terminating in treatment agent injection ports proximate the elevation of said drilling section for conveying treatment agents from the earth surface to said injection ports;

e) means affixed to said casing for sensing hazardous waste contaminants proximate the drilling section and for transmitting information to a location proximate the second end of the kelly bar, said drilling section being sized to bore a hole larger than the cross section of said casing; and f) means for automatically controlling the type and amount of remediation agents to be conveyed through said conduit to be injected into said waste proximate the elevation of said drilling section dependent upon the spectroscopic analysis of contaminants and treatment progress at the subsurface elevation.

DESCRIPTION OF THE PREFERRED EMBODIMENTS

Figure 1:
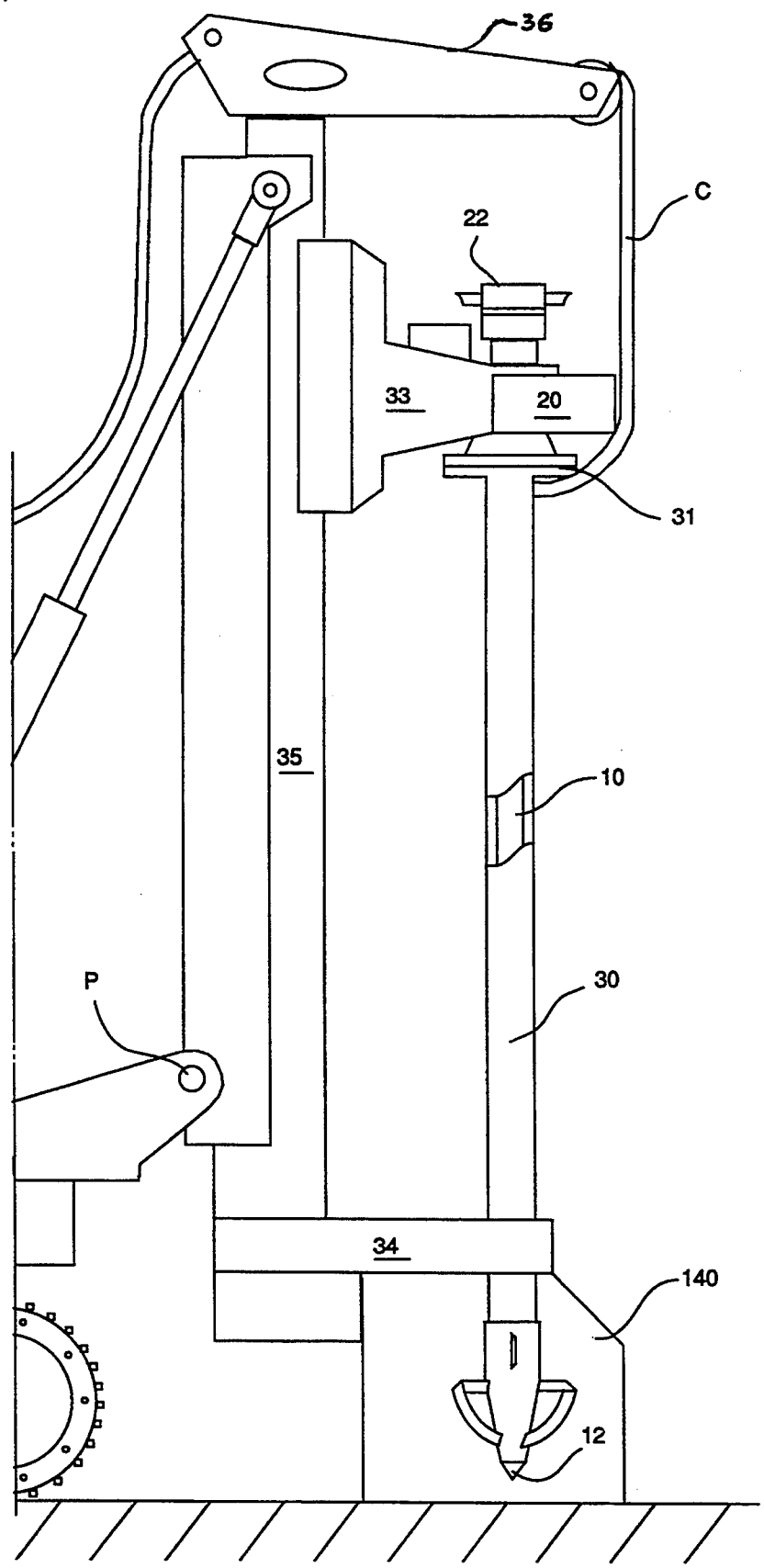
FIG. 1 is a schematic elevation of the present invention pivotally mounted on a tracked vehicle, shown in part.

Throughout the following detailed description, the same reference numerals will be used to describe the same parts of the invention.

Figures 2, 3:
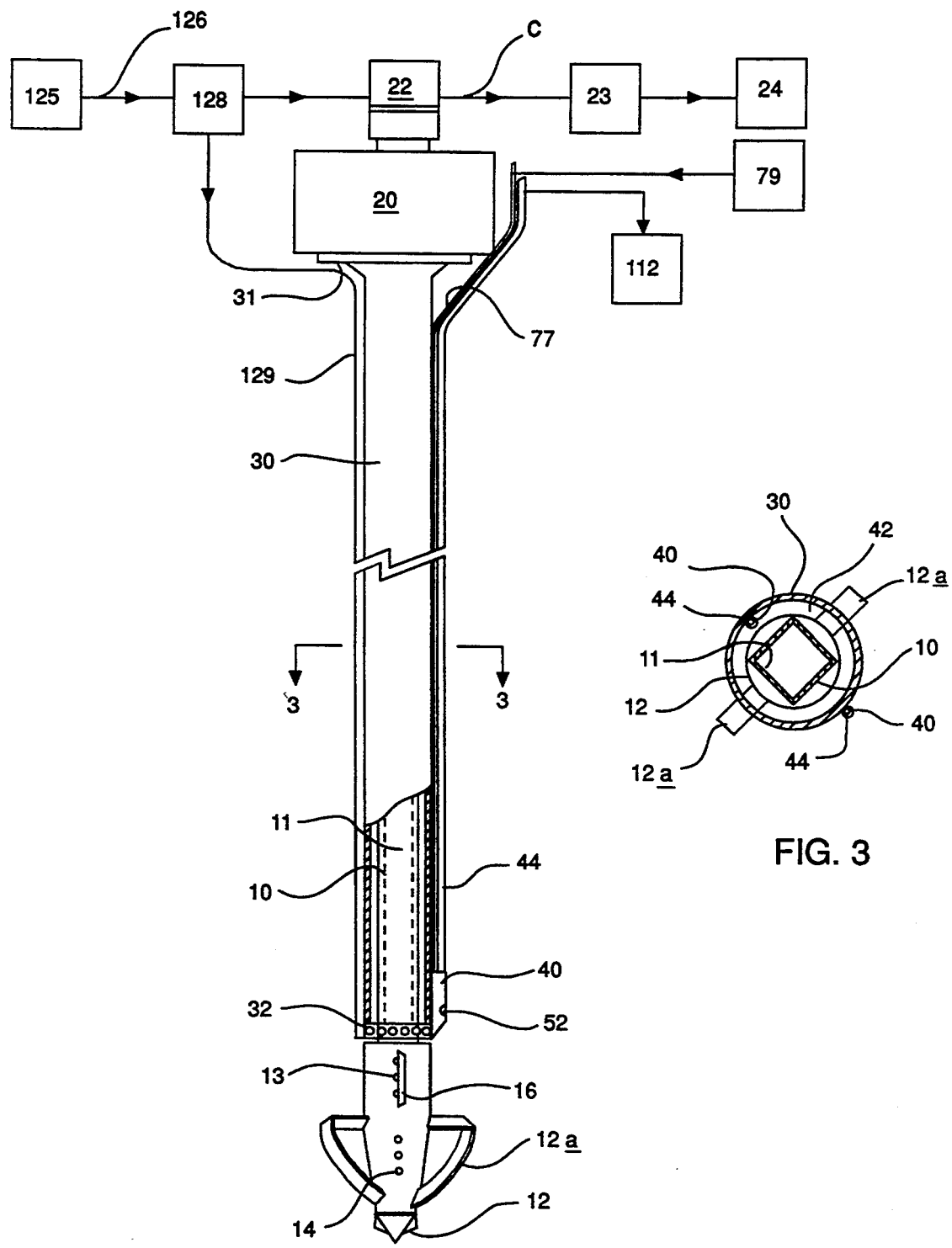
FIG. 2 is a schematic view of the invention, partly in cross section.
FIG. 3 is a cross section taken at line 3—3 on FIG. 2 showing placement of probes both outside of the drill casing and inside of the drill casing in an annular clearance space between the interior of the casing and a rotatable kelly bar therein.

FIG. 1 shows a characterizer and remediation system comprising an elongate rotatable kelly bar 10 having a drilling section comprising a fixed blade drill bit 12 rigidly affixed to the lower end thereof. The kelly bar 10 ordinarily has a cross-section of noncircular configuration (FIG. 3) so that it can be driven by a conventional top drive motor 20. The kelly bar 10 is preferably hollow and its internal passageway 11 seen in FIG. 3 comprises a dual purpose conduit for either removing vaporized or gaseous materials from soil gas inlet ports 13 which extend through the wall of the drill bit to the hollow interior thereof, the ports 13 being located at a subsurface location proximate the drilling section bit 12 to pass soil gas upwardly through the kelly bar 10 to a fluid swivel 22 located above the top drive motor 20 or for downwardly conveying treatment reagents to be injected through reagent injection ports 14 (FIG. 2). Subsurface originating gases and vapors are conducted upwardly through the interior of hollow kelly bar 10 and swivel 22 or through a clearance space 42 between kelly bar 10 and casing 30 via bundled conduit C to a surface location proximate the upper end of the kelly bar 10 where they may be analyzed by suitable equipment (FIG. 2) at the surface. The surface equipment typically includes a vacuum pump 23 to assist gas removal, and gas analytical devices 24. Ports 13 and 14 are located proximate the drilling section and, as referred to herein, the term "proximate the drilling section" is intended to mean that the ports are disposed in the general zone of mixing of materials by the cutters or bit or slightly thereabove such that gases may be conveyed upwardly via the ports 13 and preferably through hollow kelly bar passageway 11 to the surface where they may be physically analyzed and, if desired, so that treatment reagents may be delivered downwardly through the kelly bar passageway 11 and ports 14 to soil at essentially the same elevation. A port blinder shield 16 is welded in the region shown to the kelly bar 10 or drill bit 12 as the case may be, directly leading the soil gas inlet ports 13 in direction of rotation to prevent or minimize clogging of the ports 13 with the churned soil as it flows over the ports 13.

The casing 30 is a non-rotating casing which contains the kelly bar 10 therein, the casing 30 being supported at its upper end by a flange 31 which is bolted or otherwise connected to the top drive motor 20 and at its lower end kelly bar 10 is centered in casing 30 by a sealed bearing 32. Intermediate spacer bearings may also be located between the kelly bar 10 and casing 30 if necessary.

The drill rig comprising the kelly bar 10, drill bit 12 and casing 30 is part of an assembly which is pivotally mounted (P) on a mobile vehicle, the assembly having an upstanding guide rail 35 to which is affixed a powered vertically moveable top motor support 33 which is power driven to move up and down on the guide rail 35 and a stationary bottom guide 34 rigidly affixed to the guide rail 35 through which the casing 30 and kelly bar 10 therein slideably moves during its vertical movement. The top drive motor 20 is rigidly affixed to the vertically moveable support 33 and is bolted or otherwise connected to a welded flange 31 on the upper end of casing 30 to support casing 30 during movement thereof vertically into and out of the ground.

It will be noted that the radial extent of the blades 12a of drilling bit 12 is at least slightly greater than the diameter of the casing 30 such that the drill bit 12 creates a bore of sufficient size to accommodate the casing 30 and an optical probe or multiple probes 40 at the lower end of the casing 30 and attached fiber optic cable 44 removably affixed to the exterior of the casing 30 by suitable means such as by welding. Optionally, the probe 40 could be mounted instead in the inside of the casing 30 as seen in FIG. 3 provided that a sufficient annular clearance space 42 is provided for the rotating kelly bar 10. Either external or internal mounted probes or both can of course be utilized in selected applications although it is presently contemplated that the external mounting is preferred since internally mounted probes are comparatively inaccessible and would require modification of the bearings 32 between the casing 30 and rotating kelly bar 10 to accommodate the probe 40 and a fiber optic cable 44 leading therefrom to the surface location.

Figure 4:
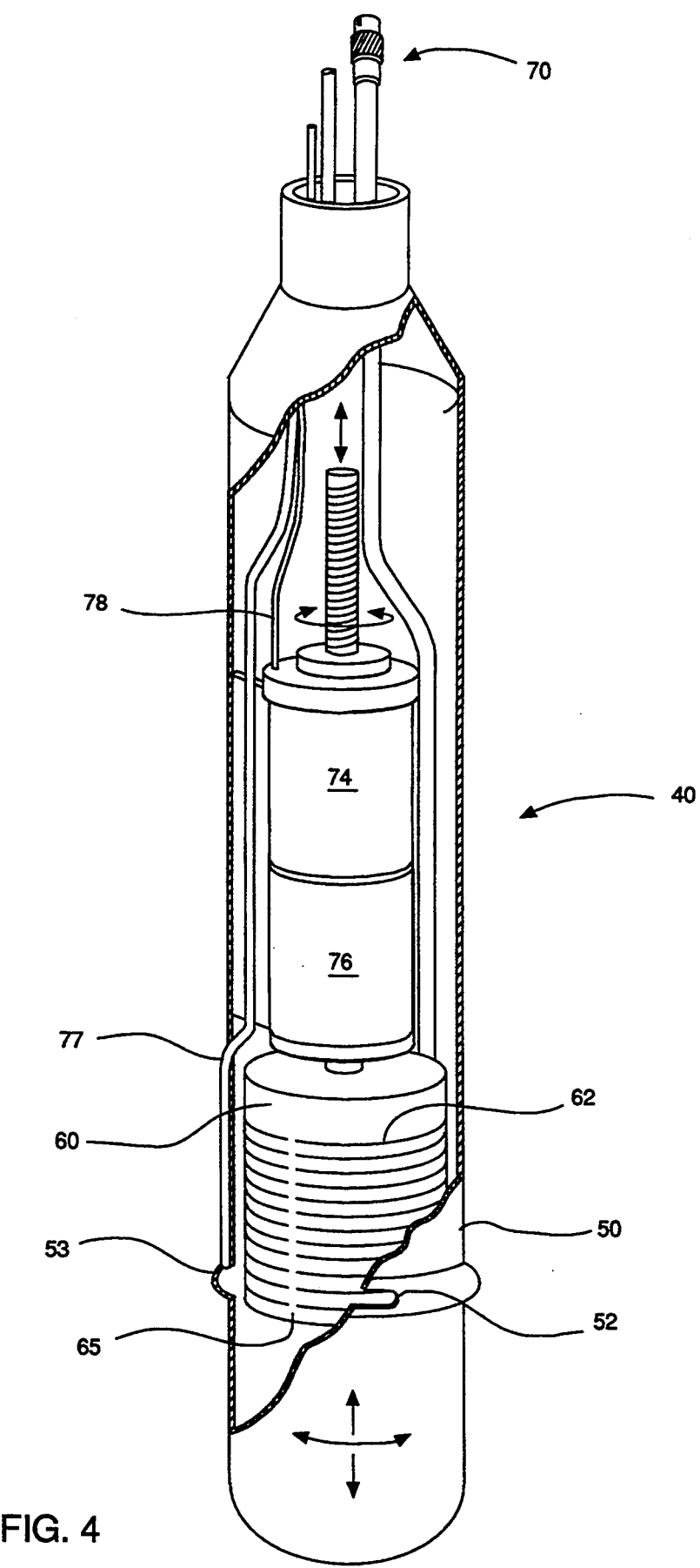
FIG. 4 is an enlarged view of an optical probe which may include multiple optical fibers useful in various embodiments of the invention.
Figure 5:
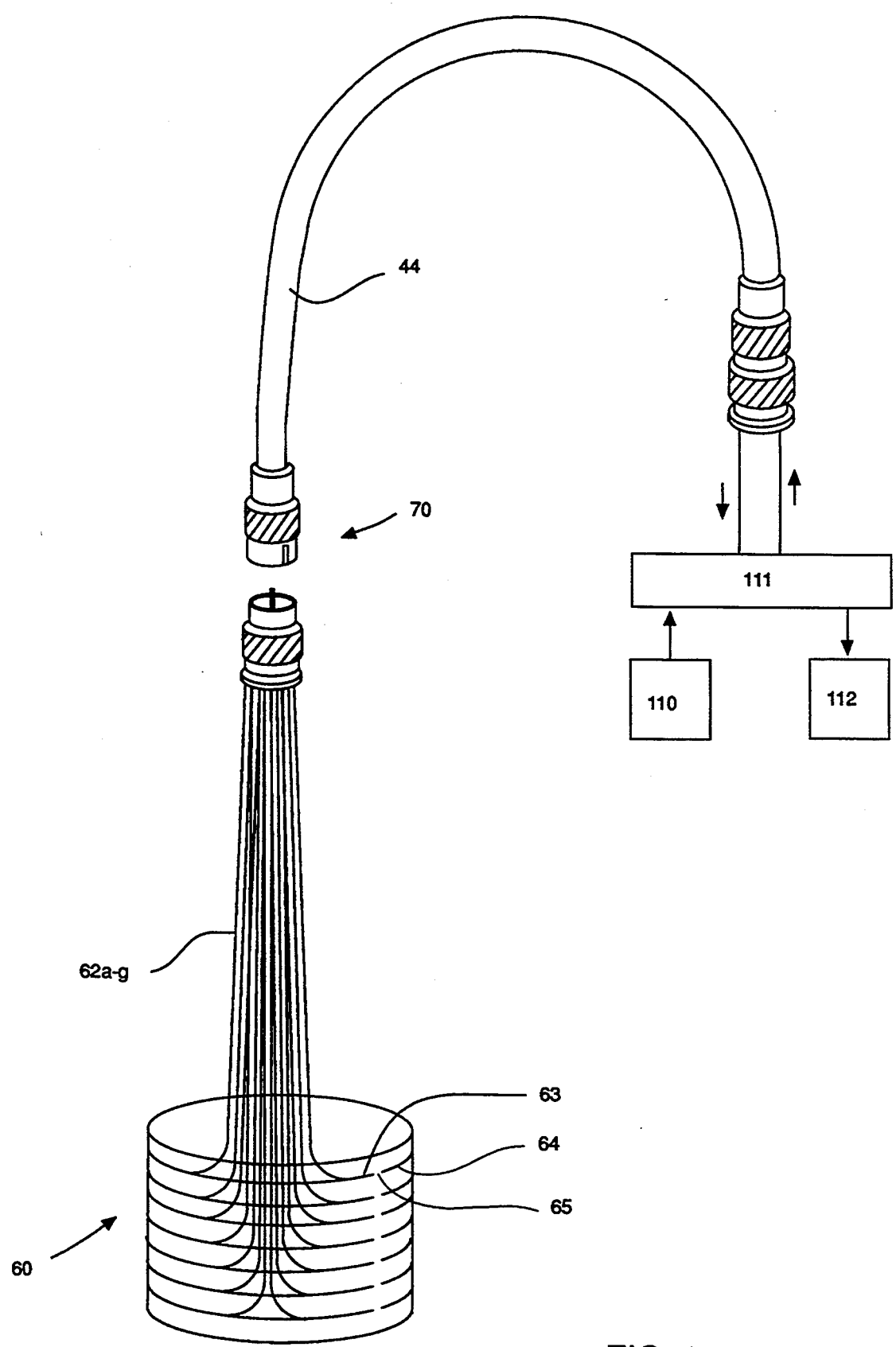
FIG. 5 is a perspective view of optical fibers mounted on a replaceable optical tube inside the casing of the probe of FIG. 3.

One form of probe 40 shown in FIG. 4 comprises a rigid protective probe housing 50 having an open exposed sample window 52 extending through the peripheral wall thereof near the lower end of the probe. FIG. 5 shows an optical tube 60 of generally cylindrical configuration used for fiber optic positioning which is slideably mounted inside the probe housing 50. The tube 60 has a plurality of optical fibers 62 wound therearound which are preferably arranged in separate spaced horizontal layers 62a-62g laid in protective grooves extending circumferentially around the tube 60. Each fiber 62 has an optical gap 65, which may be of various sizes, therein between first and second ends 63, 64 which extend upwardly to a multi-fiber optic coupling 70 which binds the individual fibers into the fiber optic cable 44 which extends upwardly from the probe housing 50 to the surface elevation proximate the drive motor 20 as seen in FIG. 2. As seen in FIG. 5, the optical tube 60 is removable from the probe housing 50 as a unit for replacement as the optical fibers 62 become chemically exposed or damaged and are no longer reliable for further use.

Means are provided for moving individual fibers and their optical gaps 65 into operative proximity with the sample window 52 in the probe housing 50. FIG. 4 shows separate vertical positioning and rotational positioning motors 74, 76 and electrical leads 78 for moving the individual fibers and gaps 65 therein toward and away from the window 52 either by vertically moving the tube 60 or by rotating the tube relative to the window 52. Although only one such positioning motor is required, two are shown. The individual fibers 62 may be arranged axially of the tube as will be seen below in an optical casing embodiment described with reference to FIG. 6, rather than circumferentially thereof in which instance the tube rotating motor 76 is employed to properly position one or more fibers and gaps 65 proximate the sample window 52. The mechanical connections of the motors 74 and/or 76 to the tube 60 will be readily apparent to those skilled in the art.

Since the probes 40 are subjected to a hostile drilling and mixing environment, the window 52 and the optical gaps 65 may frequently become clogged with solid materials therefore preventing further sensing of fluid materials in the optical gaps 65 where they can be analyzed. To alleviate this problem, a close spacing is maintained between the optical tube 60 and the housing 50 and a pressurized fluid flushing nozzle may be positioned near the probe window 52 to flush it as necessary. As seen in FIGS. 2 and 3, one means of flushing the probe window 52 and the optical fibers and gaps 65 comprises a fluid pump 79 (preferably water) and a fluid jetting tube 77 extending on the exterior of drill casing 30 down to the probe housing 50 where it is placed in fluid communication with an annularly extending cleaning chamber 53 in the wall of the probe housing 50. The injected cleaning fluid passes over an optical gap or gaps 65 and exits the housing 50 through the sample window 52 to flush it of accumulated foreign material.

Figure 6:
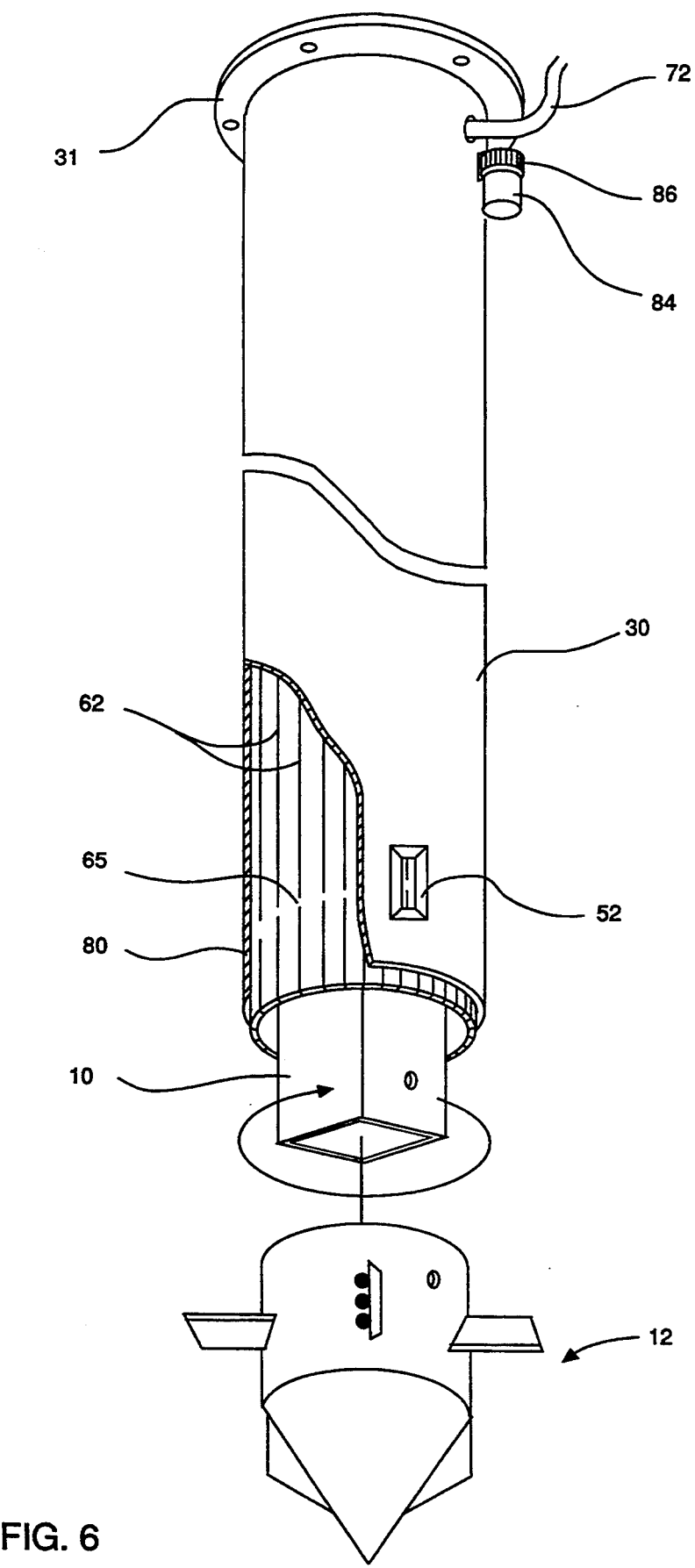
FIG. 6 is a schematic elevation of an embodiment of the invention employing an optical casing slideably mounted inside of an enclosing drill casing having an optical port therein and partly broken away to show the optical fiber routing on the optical casing.

Referring now to FIG. 6, a modified embodiment of the invention employing an optical casing 80 mounted inside the casing 30 for movement relative thereto is disclosed. The optical casing 80 is disposed in annular clearance space 42 (FIG. 3) between the rotating kelly bar 10 and the non-rotating casing 30 and comprises an elongated tube having a plurality of discrete optical fibers 62 axially wound them around with optical gaps 65 on the exterior surface of the optical casing 80 at an elevation proximate the drill bit 12 or mixing blades so that the individual optical gaps 65 can be selectively aligned with a sampling port 52 extending through the drill casing 30. The individual ends of the various optical fibers 62 are bundled together as was described with reference to FIG. 5 into a fiber optic cable 72 and an electric or pressure driven motor 84 and drive wheel 86 is shown for rotating the optical casing 80 relative to the drill casing 30 and sampling port 52 therein. The fibers are recessed in the exterior annular surface of optical casing 80 to prevent damage by the drive wheel 86.

Figures 7A, 7B, 7C, 7D:
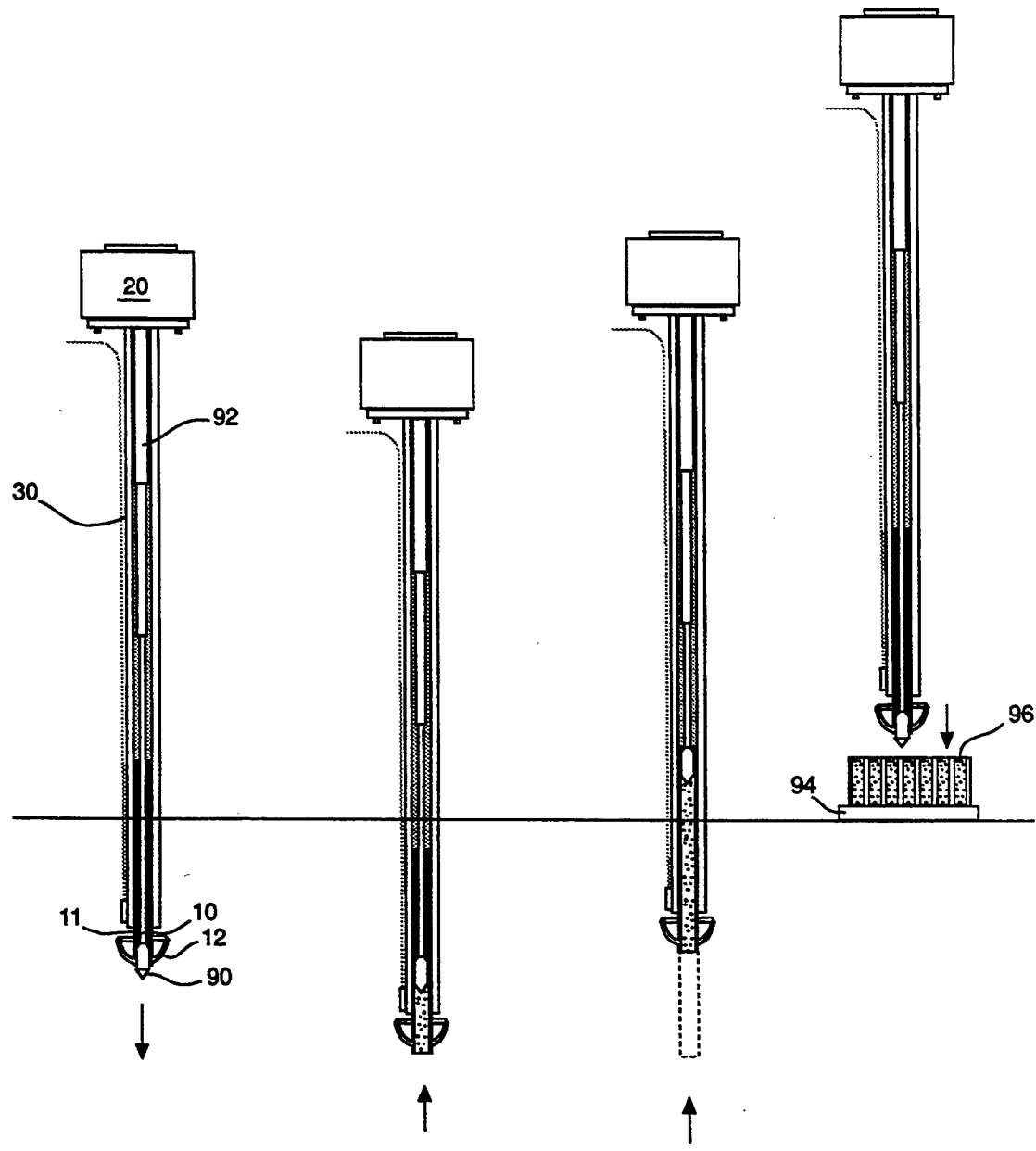
FIGS. 7a-7d comprise schematic elevations of the preceding embodiments of the invention employing a hollow kelly bar modified to incorporate a soil core sampler therein and sequentially showing the steps of extraction and storage of a core sample.

Since in situ conditions and analysis of the fluids present in the optical gaps often indicate that analysis of solid samples may be necessary or beneficial, a solid soil core sampling apparatus is optionally provided inside the hollow kelly bar 10 inside the casing 30 as seen in FIGS. 7a–7d. The solid soil sampling apparatus comprises a generally conical drive point 90 slideably mounted inside a circular kelly bar bore 11 which also serves as a soil sample core barrel. If desired, a separate core barrel liner (not shown) may be used in the kelly bar 10. The drive point 90 is affixed to a linear actuator 92 such as a hydraulic cylinder/piston arrangement controllable from the surface location. The actuator 92 is initially in a fully extended position and the top drive motor 20, non-rotatable casing 30 and actuator 92 are then moved together downwardly at the rate of boring. The drive point 90 is thus moved downwardly with the coring bit 12 to a selected elevation A (which is a fixed distance depending upon the selected length of the core sample) above the subsurface elevation B from which the soil sample is taken. The linear actuator 92 retracts as it holds the core point 90 at this elevation A during further penetration of the earth by the coring bit 12 during which time the soil sample automatically enters the kelly bar/core barrel as seen in FIG. 7b. To retrieve the sample, the kelly bar 10, casing 30 and solid soil sample retained therein is withdrawn from the subsurface as seen in FIG. 7c and is positioned above a soil sample retainer 94 following which the linear actuator 92 is extended forcing the conical sample point 90 to eject the sample or portions thereof from the kelly bar/core barrel directly into receptacles 96 in the sample retainer 94 without human handling or exposure of the sample to the ambient atmosphere (FIG. 7d) thereby preventing release of soil gas from the core sample. The sample may be separated into discrete sections and frozen in the various receptacles 96.

As will be appreciated by persons skilled in the art, each optical fiber 62 is energized by a light source 110 shown schematically in FIG. 5 such that the light is conducted through a multiplexer 111 by the fiber to and across the optical gap 65 therein and is subsequently returned via the multiplexer 111 to a spectroscopic analyzer 112. As used herein, the term "spectroscopic analyzer" is intended to comprise a general term for analytical instruments including photodetectors such as spectrographs, spectrometers and the like which analyze light patterns and the modulation thereof by vapors or gases entering the optical gap 65 to determine the composition and/or concentration of fluids present in the optical gap 65. It will also be appreciated that the optical gap may be a transmissive gap or a reflective gap or, in general, any optical gap between the ends of a transmissive optical fiber 62 of dimensions suitable for analyzing contaminants.

Figure 8:
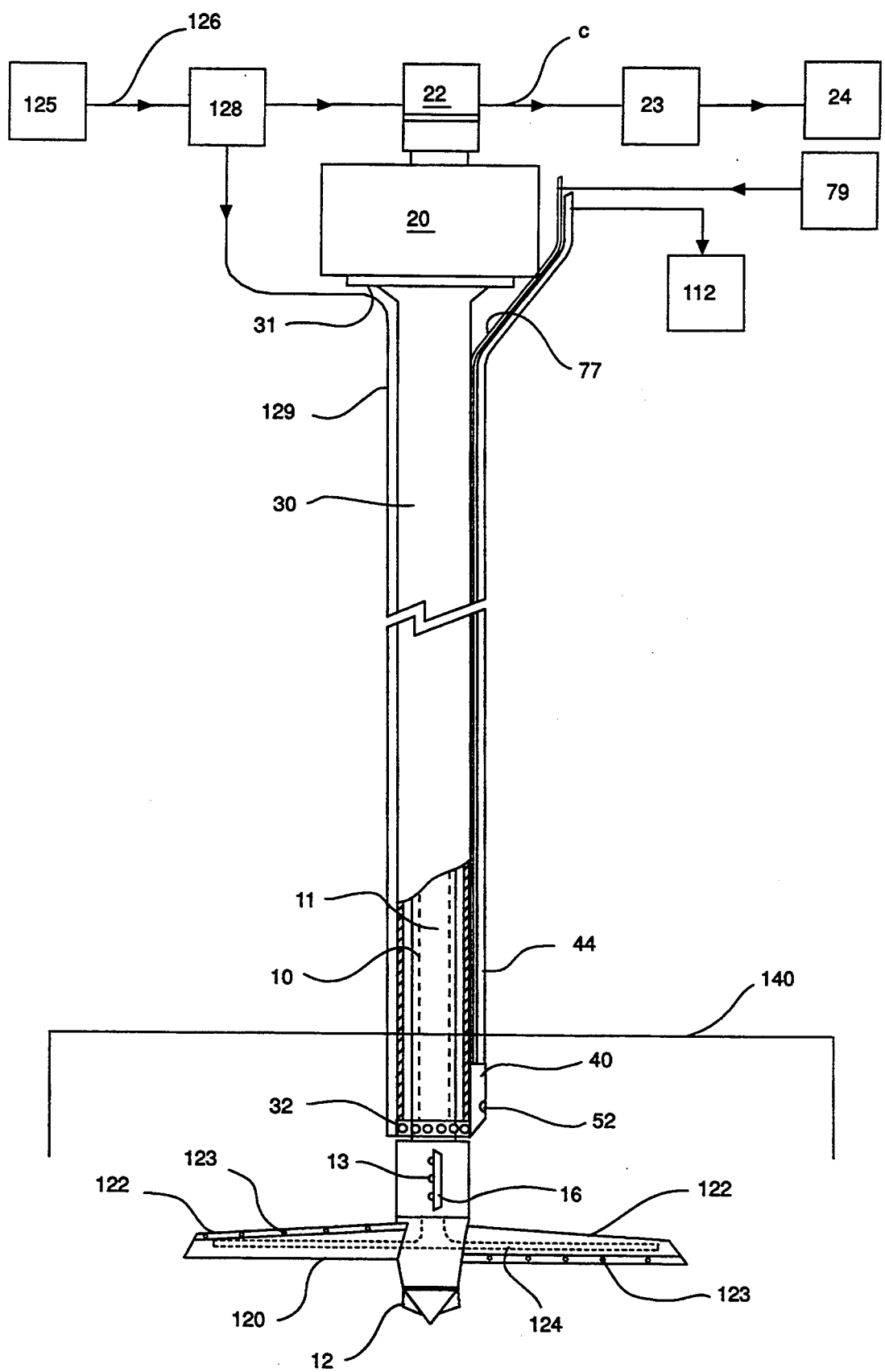
FIG. 8 shows a modified drilling section bit in the form of a chemical injection and mixing blade substituted for the drill bit shown in FIG. 1.

Although, in its broadest aspects, the invention comprises means for delivering analytical equipment to and retrieving analytical equipment from a subsurface location and for retrieving data therefrom, in its most important aspects, the analysis is intended primarily to comprise the "eyes and ears" of hazardous waste detection and treatment during a soil remediation process. Therefore, as seen in FIG. 8 the drill bit 12 may take the configuration of a solid elongated mixing bit 120 having a plurality of evenly radially distributed hollow blades 122 each provided with injection ports 123 for dispersing hot air, steam or treatment reagents into contaminated sites to be remediated. Reagents to be injected are conveyed downwardly through the interior passageway 11 of hollow kelly bar 10 and elongate internal passageways 124 in or upon the mixing blades 122 for ejection at the ports 123. Reagents to be injected are conveyed from suitable surface located external sources 125 through fluid supply tubing 126 which enters the upper stationary portion of fluid swivel 22 which has its lower rotatable portion rigidly affixed to the upper end of the kelly bar 10 whereby the reagents will be conveyed downwardly through the internal passageway 11 of the kelly bar 10 to the elevation of the mixing bit 120. Alternatively, reagents from source 125 may be directed by a pump 128 and conduit 129 mounted exteriorly on casing 30 to a discharge nozzle located at the elevation of the drill bit 120.

Figure 9:
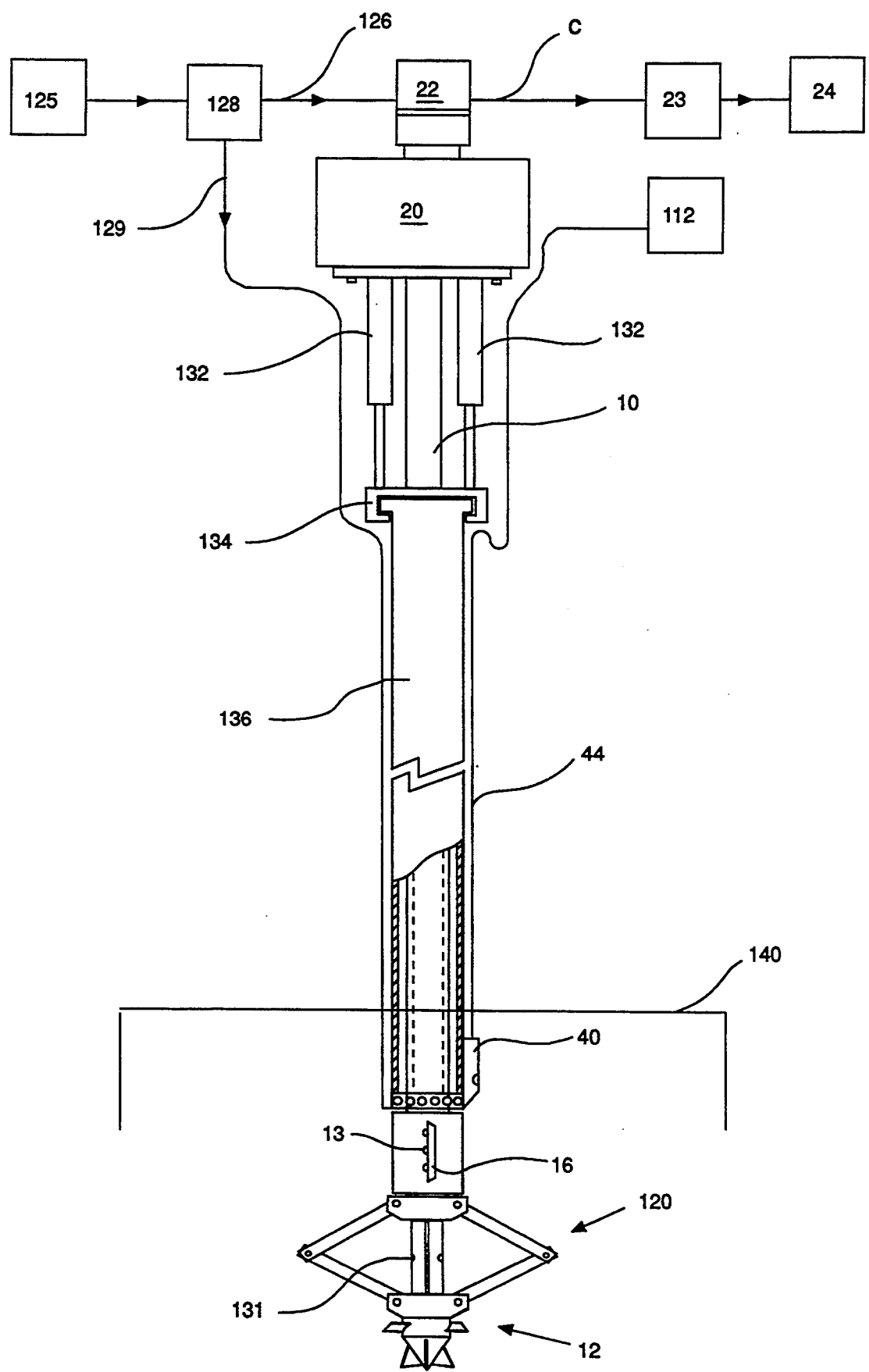
FIG. 9 shows a a radially expansible and contractible drilling section which is especially useful for site remediation, the device having a folding underreamer.

The embodiment of the invention shown in FIG. 9 is particularly useful for remediating selected soil depths which may not be contaminated thereabove or underground storage tanks and the like which have a relatively small access port or a small opening in the soil is desired. As shown, the device comprises a rotatable kelly bar 10 with a top drive motor 20 and multi-port fluid swivel 22 which receives treatment reagents from suitable external supplies. Fluid reagents under high pressure are conveyed from source 125 via pump 128 and swivel 22 downwardly through the kelly bar 10 to the treatment elevation at which the drilling section includes radially directed high pressure jet nozzles 131 and a folding underreamer 120 attached to the kelly bar 10. The underreamer 120 can be radially deployed at the desired treatment elevation. Deployment can be gradual as the underreamer 120 is repeatedly moved between two vertically spaced locations to create a moveable waste treatment zone. Gradual deployment of the underreamer 120 results in significantly reduced motor torque requirements as remediation takes place. As the device reaches the selected soil elevation or is inserted into the access opening of the underground tank, high pressure fluid jetting is commenced and linear actuators such as hydraulic piston/cylinder units 132 are actuated to extend the underreamer 120 by downwardly pushing a cap 134 and non-rotatable casing in the form of an actuator tube 136 which is positioned above the rotatable underreamer 120 for increasing the radial extent of the underreamer 120 for treatment. The high pressure jetting of treatment reagents assists in deployment of the underreamer 120. Soil is treated vertically and horizontally by increasing or decreasing the radial extent of the underreamer 120. One or more optical probes 40 as described above may be affixed to the exterior of the non-rotatable actuator tube 136 which is the mechanical equivalent of the casing 30 shown in the embodiment which does not use an underreamer.

Figure 10:
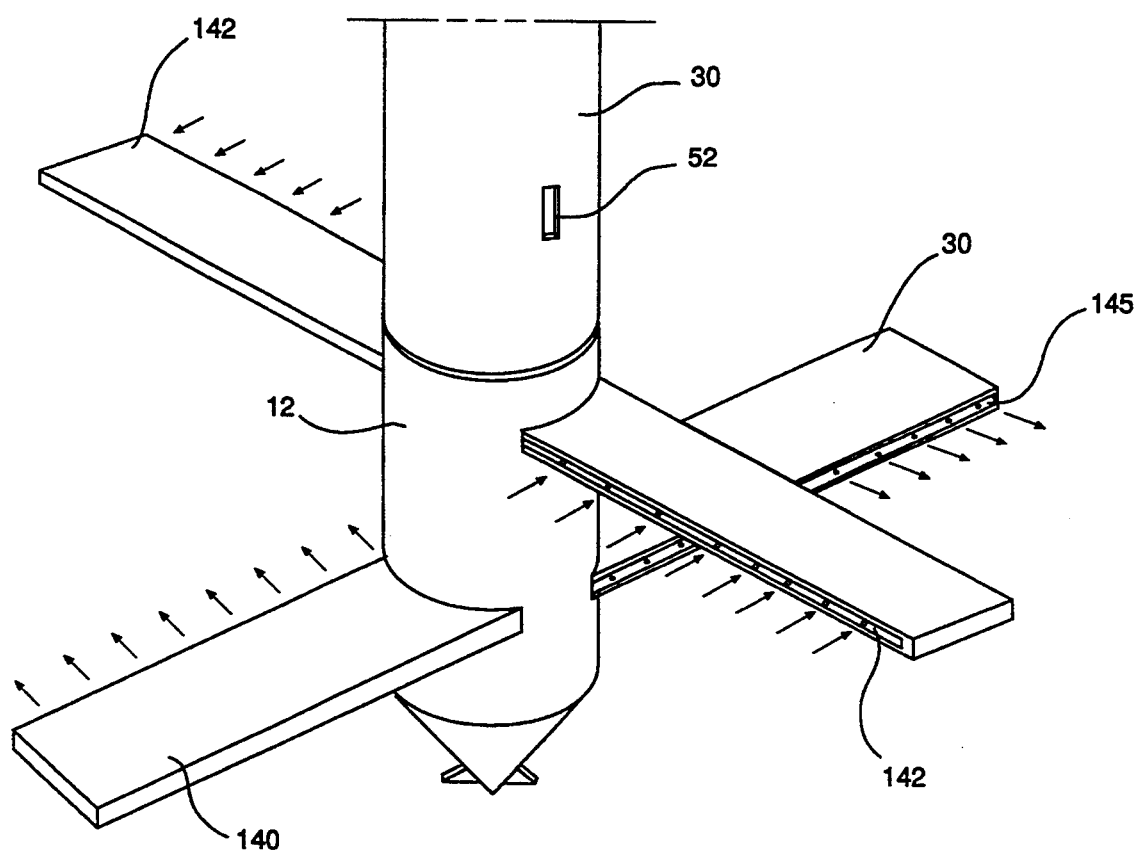
FIG. 10 is a schematic perspective view of a fixed blade drilling section having vertically spaced sets of injector and contaminant removal cutters.
Figure 11:
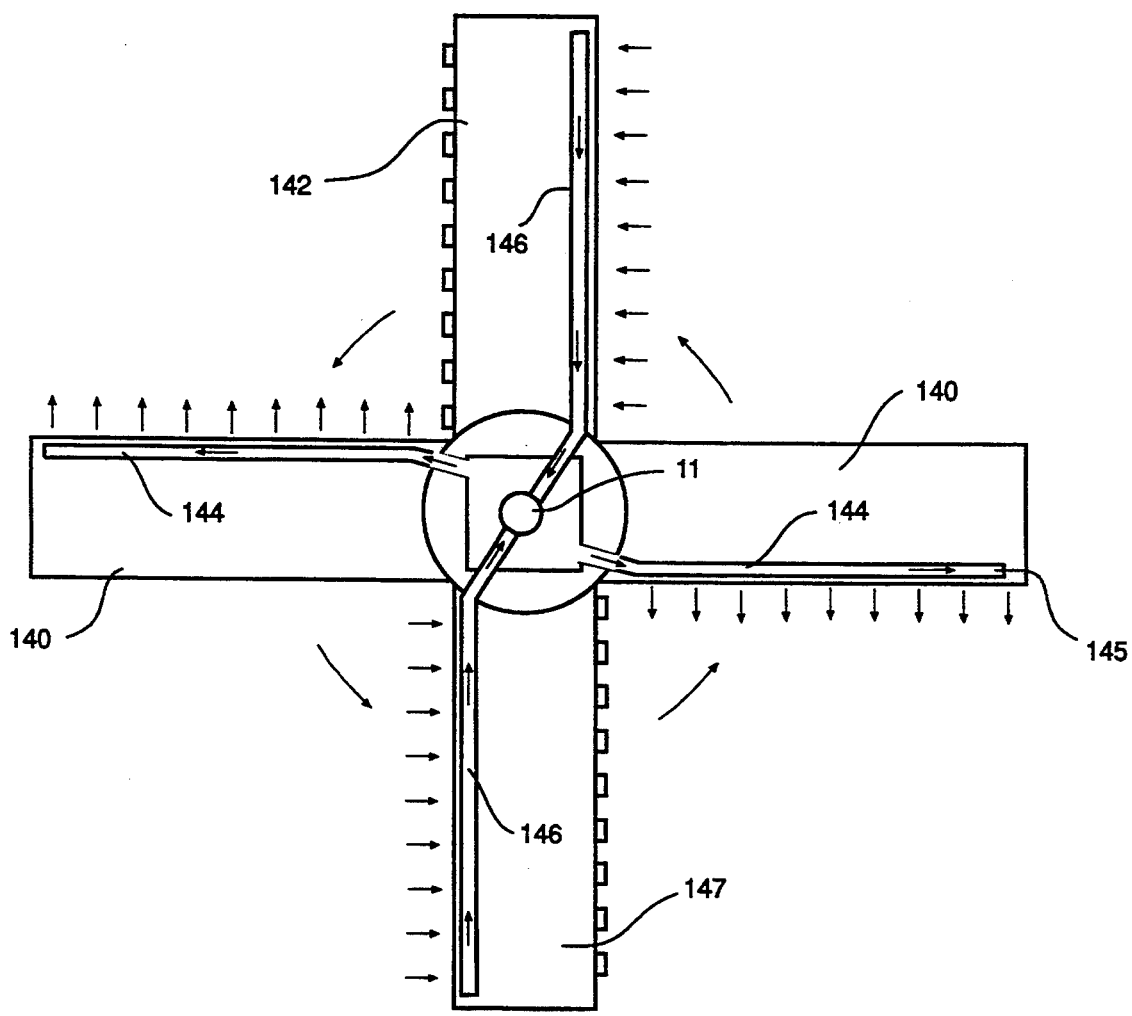
FIG. 11 is a schematic plan view of FIG. 10.
Figure 12:
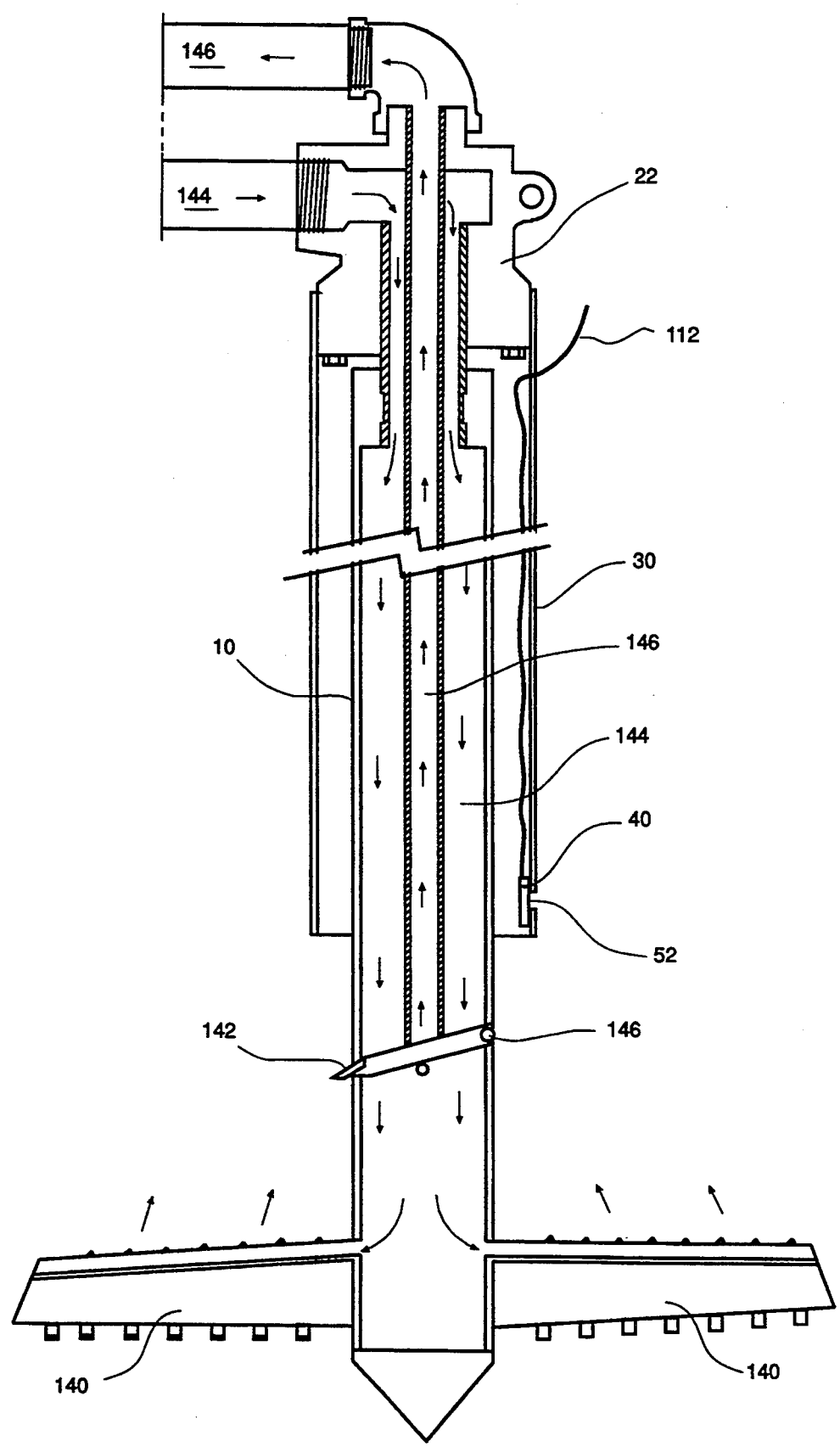
FIG. 12 is a schematic cross-section elevation of the embodiment of FIG. 10.

The drilling section embodiment shown in FIGS. 10–12 is a fixed blade cutter arrangement instead of a folding underreamer as described previously. Two vertically spaced sets of cutter blades 140, 142 each having fluid conduits 144, 146 therein are mounted on the lower end of the kelly bar proximate the lower sensing end of casing 30. The lower set of blades 140 carries contaminant treatment fluid conduits 144 which terminate in a plurality of injection nozzles 145. The upper set of blades 142 carries the conduits 146 for removing volatilized contaminants from the waste treatment zone. Each set of conduits 144, 146 separately continues and extends upwardly through the kelly bar as seen in FIG. 12 to an above ground location where the conduit 146 discharges to 24 (FIG. 2) and from where the conduit 144 receives a supply of contaminant treatment fluid to be injected into the contaminated soil. As used herein, the term "treatment fluid" is intended in its broadest sense to include, but not be limited to, e.g. heated fluids such as steam or hot air, wet and flowable dry granulated chemical or biological reagents and microbes, biological nutrients and the like.

A typical hazardous waste disposal site remediation is a complex operation involving repeated analysis and remediation steps. With the present invention, these steps need not be intermittent and instead are simultaneous—i.e., in real time during a single drilling stage. During the drilling and chemical injection, analytical data is continually transmitted to the analyzing apparatus 112 at the surface which is combined with 3-D mapping of the contamination profile and remediation progress of the contaminated site. Optical sampling as well as gas sampling can be conducted simultaneously. The injection of suitable remediation agents can be varied as necessary depending upon the sensed conditions whereby remediation of non-contaminated areas can be prevented or minimized and the most efficient use of the required treatment reagents without exceeding the necessary volumes thereof for effective treatment can be carefully controlled to result in the most economical treatment of a site. When the internal passageway 11 of the kelly bar 10 is not being used for delivery of treatment reagents it can be used to retrieve soil gases to the surface elevation where physical analysis of the gas may be used as a cross check to validate the data simultaneously obtained by the optical analysis.

During on site setup of the apparatus, a confined space or enclosure is created in the area immediately surrounding the borehole by a gas and vapor impermeable shroud or process module 140 having its interior maintained under subatmospheric pressure so that contaminant vapors and gases escaping from the borehole are immediately decontaminated by scrubbers mounted on the process module 140 and do not contaminate the atmosphere or endanger personnel at the site.

Persons skilled in the art will readily appreciate that various modifications can be made from the preferred embodiments disclosed herein and thus the scope of protection is intended to be defined only by the limitations of the appended claims.

I claim:

1. A method of identifying hazardous waste in a subsurface soil site comprising the steps of:
    a) positioning contaminant sensing means proximate a sensing end of a nonrotatable drill casing having a first diameter;
    b) boring a hole into the hazardous site using a rotary drill comprising a rotary kelly bar and a drilling section affixed to said kelly bar which creates a hole of a second diameter larger than said first diameter;
    c) longitudinally inserting said sensing end of said non-rotatable casing and contaminant sensing means into said hole while boring said hole; and
    d) using said contaminant sensing means to sense the presence and composition of soil contaminants encountered during said boring of said hole while logging the characteristics of said contaminants and the locations at which they were encountered.

2. The method of claim 1, further comprising the step of heating the soil proximate said sensing end of said casing to volatilize volatile contaminants in the site.

3. The method of claim 2, further comprising the step of removing volatilized contaminants from the location at which they were encountered through said casing to an enclosure remote from the location at which they were encountered.

4. The method of claim 2, further comprising the step of removing volatilized contaminants from the location at which they were encountered through said kelly bar to an enclosed space remote from the location at which they were encountered.

5. The method of claim 4, further comprising the step of supplying contaminant treatment fluid through said kelly bar and injecting said treatment fluid through said drilling section into contaminated soil at a location spaced from said sensing end of said casing.

6. The method of claim 5, wherein said volatile contaminants are also removed through said drilling section.

7. The method of claim 6, wherein said hole is essentially vertical and further comprising the step of injecting said treatment fluid through a lower portion of said drilling section and removing said volatilized contaminants through an upper portion of said drilling section to an enclosure for treatment.

8. The method of claim 1, wherein said drilling section is radially expansible and is used to bore a hole of said second diameter to a first location at which hazardous waste is to be examined and treated and further including the steps of: injecting contaminant treatment fluid into the contaminated soil while axially moving said radially expansible drilling section from said first location to a second location at which contaminants are encountered; radially expanding said drilling section while moving said section from said first location to said second location to increase the diameter of said hole between said first and second locations.

9. The method of claim 8, further comprising the step of supplying contaminant treatment fluid through said kelly bar and injecting said treatment fluid into contaminated soil at a location spaced from the end of said casing.

10. The method of claim 9, further comprising the steps of repeatedly raising and lowering said drilling section between said first and second locations while progressively radially expanding said drilling section, injecting treatment fluid and removing volatilized contaminants.

11. The method of claim 10, further comprising the step of heating the soil proximate said sensing end of said casing by injecting heated fluid into said hole to volatilize volatile contaminants in the site.

12. The method of claim 11, further comprising the step of removing volatized contaminants from the location at which they were encountered to an enclosure remote from the location at which they were encountered through a first conduit and wherein said treatment fluid is supplied through a second conduit.

13. The method of claim 12, wherein said second conduit is in said kelly bar and said first conduit is in said casing.

14. The method of claim 12, wherein said radially expansible drill section is expanded and contracted by axially moving said non-rotatable casing.

15. The method of claim 14, further comprising the step of decreasing the diameter of said radially expansible drilling section at a third location proximate the soil surface and removing said drilling section through a section of the hole which remains at said first diameter.

16. A hazardous waste characterization system comprising:
  a) a soil boring apparatus which includes:
    1) a rotatable drilling section;
    2) a rotatable kelly bar having a first end affixed to said drilling section;
    3) a motor for rotating said kelly bar and said drilling section, said motor being drivingly attachable to said kelly bar proximate a second end thereof; and
    4) means for linearly moving said motor relative to a support therefor;
  b) a non-rotatable casing surrounding said kelly bar and extending substantially the length thereof between said motor and said drilling section, said casing being affixed to and supported by said means for linearly moving said motor; and
  c) means affixed to said casing for sensing hazardous waste contaminants proximate the drilling section and for transmitting information to a location proximate the second end of the kelly bar, said drilling section being sized to create a bore larger than the cross section of said casing.

17. The system of claim 16, wherein said soil boring apparatus, said casing and said means for sensing is mounted on a mobile vehicle for movement between a stowed travel position and an operative characterization position.

18. The system of claim 17, further comprising an optical light source and a spectroscopic analyser including a photodetector at said location proximate said second end of said kelly bar; said sensing means including at least one optical fiber having a first end connected to said light source, a second end connected to said analyzer and an optical gap therein for receiving fluid materials to be optically analyzed, said optical gap being located at an elevation proximate the elevation of said drill bit whereby said spectroscopic analyzer receives said transmitted information to determine the composition and/or concentration of fluid materials in said gap proximate the in situ elevation of said drill bit.

19. The characterization system of claim 18, wherein said means for sensing comprises an optical probe mounted on said non-rotatable casing, said probe having a probe housing, said optical probe casing having at least a portion of said optical fiber and said optical gap therein, and a window in said probe housing proximate said optical gap in said fiber.

20. The characterization system of claim 19, further comprising a plurality of said optical fibers each having an optical gap therein inside of said probe housing, and means for sequentially positioning selected ones of said gaps proximate said window.

21. The characterization system of claim 16, wherein said kelly bar is hollow and further comprising a plurality of soil gas removal ports proximate the elevation of said drill bit for conducting soil gas into said kelly bar and pump means for removing soil gas to the surface though the interior of said kelly bar.

22. The characterization system of claim 16, wherein said kelly bar is hollow and further comprising means mounted in said kelly bar for extracting solid soil samples taken proximate the elevation of said drill bit.

23. The characterization system of claim 22, wherein said means for extracting soil samples comprises a drive point moveable with said drill bit to an elevation above the elevation from which said soil sample is to be taken and means for holding said drive point at said selected elevation as said kelly bar and drilling bit advances to a lower elevation to permit said soil sample to enter said kelly bar as said drilling bit advances.

24. A hazardous waste characterization and soil remediation system comprising:
  a) a soil boring apparatus having a rotatable drilling section, a rotatable kelly bar having a first end affixed to said drilling section and motor means drivingly attachable to said kelly bar proximate a second end thereof for rotating said kelly bar and drilling section;

b) a non-rotatable casing surrounding said kelly bar and extending substantially the length thereof between said motor means and said drilling section, said casing being affixed to and supported by said means for rotating;

c) means for axially moving said motor means and said casing;

d) conduit means terminating in treatment agent injection ports proximate the elevation of said drilling section for conveying treatment agents from the earth surface to said injection ports;

e) means affixed to said casing for sensing hazardous waste contaminants proximate the drilling section and for transmitting information to a location proximate the second end of the kelly bar, said drilling section being sized to bore a hole larger than the cross section of said casing; and f) means for automatically controlling the type and amount of remediation agents to be conveyed through said conduit to be injected into said waste proximate the elevation of said drilling section dependent upon the spectroscopic analysis of contaminants and treatment progress at the subsurface elevation.

25. The system of claim 24, wherein said drilling section comprises a plurality of rotary cutters having said injection ports thereon and conduits in at least some of said cutters for supplying contaminant treatment to said injection ports.

26. The system of claim 25, wherein said cutters comprise a first set of generally radially extending cutters having said conduits and injection ports and a second set of generally radially extending cutters having conduits therein for removing volatilized contaminants from said site through said kelly bar.

27. The system of claim 24, wherein said drilling section comprises a radially expansible drilling section and means for selectively expanding and contracting said section during rotation of said kelly bar and drilling section.

28. The system of claim 27, wherein said means for selectively expanding and contracting includes said casing and further comprises hydraulic cylinder means affixed to said casing for axially moving said casing, said casing having a sensing end which is engageable with an axially moveable portion of said drilling section.

29. The system of claim 28, further comprising an optical light source and a spectroscopic analyser including a photodetector at said location proximate said second end of said kelly bar; and said sensing means including at least one optical fiber having a first end connected to said light source, a second end connected to said analyzer and an optical gap therein at an elevation proximate said drill bit for receiving fluid contaminants to be optically analyzed in situ, whereby said spectroscopic analyzer receives said transmitted information to determine the type and/or concentration of contaminants in said gap.

30. The system of claim 29, wherein said means for sensing comprises an optical probe mounted on said casing, said probe having a probe housing, said optical probe housing having at least a portion of said optical fiber and said optical gap therein, and a window in said probe housing proximate said optical gap in said fiber.

31. The system of claim 30, further comprising a plurality of said optical fibers each having an optical gap therein inside of said probe housing, and means for sequentially positioning selected ones of said optical fiber gaps proximate said window.

32. The system of claim 31, wherein said fibers and gaps are mounted around a generally cylindrical tube, said tube and fibers being removable from said probe as a unit for replacement.

33. The system of claim 32, wherein said means for positioning said fiber optical gaps comprises means for axially moving said tube and fiber optical gaps relative to said window.

34. The system of claim 33, wherein said means for positioning said gaps comprises means for rotating said tube and fiber optical gaps relative to said window.

35. The system of claim 30, wherein at least one said probe is mounted on the exterior of said non-rotatable casing, said drill bit having a radial extent which exceeds the radius of said casing to provide a bore sufficiently large to receive said externally mounted probe.

36. The system of claim 35, further comprising means for flushing said window with pressurized fluid to remove adhered materials therefrom.

37. The system of claim 30, further comprising an annular clearance space between said non-rotatable casing and said rotatable kelly bar, said casing having a port therein which opens to said annular clearance space, and at least one said probe is mounted in said clearance space with said probe window being aligned with said casing port.

38. The system of claim 28, wherein said non-rotatable casing has an optical port extending therethrough, a generally cylindrical optical casing mounted in said non-rotatable casing for movement relative thereto, a plurality of said optical fibers and optical gaps on said optical casing, and means for moving said optical casing relative to said non-rotatable casing to position selected ones of said optical gaps proximate said optical port.

39. The system of claim 38, wherein said means for moving said optical casing relative to said non-rotatable casing comprises means for rotating said optical casing.

40. The system of claim 28, further comprising means mounted in said kelly bar for extracting solid soil samples taken proximate the elevation of said drill bit.

41. The system of claim 40, wherein said means for extracting soil samples comprises a drive point moveable with said drill bit to an elevation above the elevation from which said soil sample is to be taken and means for holding said drive point at said selected elevation as said drilling bit advances to a lower elevation to permit said soil sample to enter said kelly bar as said drilling bit advances.

42. The system of claim 41, wherein said means for holding said drive point includes fluid actuator means, said fluid actuator means being actuatable to remove said soil sample from said kelly bar.

* * * * *